United States Patent [19]

Humbert et al.

[11] Patent Number: 4,556,736
[45] Date of Patent: Dec. 3, 1985

[54] METHOD FOR PRODUCING CRYSTALLINE ACRYLAMIDO ALKYL TRIALKYLAMMONIUM CHLORIDES

[75] Inventors: Heiko Humbert, Hamburg; Karlheinz Laping, Moers, both of Fed. Rep. of Germany

[73] Assignee: Deutsch Texaco Aktiengesellschaft, Hamburg, Fed. Rep. of Germany

[21] Appl. No.: 635,685

[22] Filed: Jul. 30, 1984

[30] Foreign Application Priority Data

Aug. 23, 1985 [DE] Fed. Rep. of Germany ....... 3330326

[51] Int. Cl.[4] .................... C07C 85/00; C07C 85/26
[52] U.S. Cl. .................................................. 564/204
[58] Field of Search ........................................ 564/204

[56] References Cited

U.S. PATENT DOCUMENTS 3,709,903  1/1973  Jefferies et al. ............... 564/204 X
3,962,332  6/1976  Trapasso ........................ 564/204

Primary Examiner—Paul F. Shaver
Attorney, Agent, or Firm—Robert A. Kulason; James F. Young; James J. O'Loughlin

[57] ABSTRACT

A process for producing crystalline acrylamidoalkyltrialkylammonium chloride by reacting a substituted acrylamide with methyl chloride in the presence of a reaction medium from the group consisting of acetone, methyl tert butyl ether and cyclohexane is provided.

8 Claims, No Drawings

METHOD FOR PRODUCING CRYSTALLINE ACRYLAMIDO ALKYL TRIALKYLAMMONIUM CHLORIDES

BACKGROUND OF THE INVENTION

Acrylamidoalkyl trialkylammonium chorides, such as methacrylamidopropyltrimethylammonium chloride, are important monomers for producing water-soluble cationic polymers. These are mainly used as flocculants and retention auxiliaries in the production of paper. Generally, the polymerizates produced from acrylamido- and methacrylamidoalkyltrimethylammonium chlorides are excellent flocculants and dewatering agents for waste-water purification.

Heretofore, the quaternization has been performed with methyl chloride in an aqueous solution. The ammonium chlorides thus obtained are not crystalline but are dissolved in water. The principle disadvantages of this procedure are that the conversion is usually performed at a temperature ranging from 60° C. to one that is substantially higher. Additionally, the presence of water results in undesired hydrolysis products. Another disadvantage is that the impurities in the starting monomer must be eliminated by treatment steps, such as with active carbon, in a subsequent stage of the process.

DISCLOSURE STATEMENT

German patent application Nos. OS 28 56 383 and OS 29 11 642 disclose the preparation of the noted compounds by quaternization of the amides with dimethyl sulfate in an aqueous phase resulting in the production of 60% aqueous solution of the quaternary product. The products obtained by these processes have some of the disadvantages noted above, namely undesired hydrolysis products and the need to purify the end product.

It is an object of the present invention to produce acrylamido and methacrylamidoalkyltrialkylammonium chlorides in a substantially pure crystalline form.

SUMMARY OF THE INVENTION

In accordance with this invention, crystalline acrylamido- and methacrylamidoalkyltrialkylammonium chlorides are produced by reacting a dialkylaminoalkylacrylamide or dialkylaminoalkylmethacrylamide with an alkyl chloride, such as methyl chloride, in the presence of a reaction medium from the group consisting of acetone, methyl tert. butyl ether and cyclohexane to produce the desired quaternary ammonium halide. In contrast to an aqueous based reaction, the quaternary product of the invention precipitates out of solution to produce a substantially pure crystalline quaternary ammonium chloride.

DETAILED DESCRIPTION OF THE INVENTION

The acrylamidoalkyltrialkylammonium chloride of the invention is represented by the general formula:

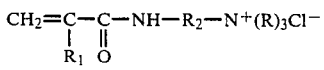

in which R is an alkyl group having from 1 to 3 carbon atoms and is preferably a methyl group, $R_1$ is hydrogen or a methyl group, and $R_2$ is a divalent hydrocarbyl radical having from 2 to 5 carbon atoms and is preferably selected from the group consisting of ethylene, propylene and 2,2-dimethylpropylene.

The quaternary salt of the invention is obtained from the reaction of a dialkylaminoalkylacrylamide represented by the formula:

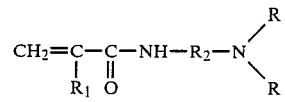

wherein R, $R_1$, and $R_2$ have the values noted above. In general, this process is conducted by reacting the prescribed dialkylaminoalkylacrylamide or dialkylaminoalkylymethacrylamide with an alkyl chloride, preferably methyl chloride, in a reaction medium from the group consisting of acetone, methyl tert. butyl ether or cyclohexane. Generally, substantially equimolar amounts of the dialkylaminoalkylacrylamide and of the alkyl chloride are employed for the reaction. However, it is preferred to employ a higher ratio of the alkyl chloride because of its high volatility. This reaction is conducted at a temperature ranging from about room temperature or ambient temperature up to the lower of the decomposition temperature of either the reactants or the product. In general, a temperature ranging from room temperature up to about 100° C. can be employed depending on the reactivity of this specific dialkylaminoalkylacrylamide starting reactant. A preferred temperature range is from about 40° C. to 80° C.

The manner of contacting the reactants is not critical. The dialkylaminoalkylacrylamide may be dissolved in the reaction medium and gaseous alkyl chloride passed into the mixture. Alternatively, a mixture of alkyl chloride, for example, e.g. methyl chloride in the reaction medium e.g. acetone in a closed reactor may be reacted by pumping the dialkylaminoalkyl acrylamide into the reactor.

The quaternary ammonium halides of the invention precipitate from the reaction solvent as they are formed. Any impurities remain dissolved in the reaction medium with the result that a highly pure crystalline product is recovered. The following examples illustrate the practice of this invention.

EXAMPLE I

Preparation of Acrylamidopropyltrimethylammonium Chloride 936 g (6 moles) of dimethylaminopropylacrylamide inhibited with 1000 ppm of di-tert. butyl cresol were dissolved in 5000 ml of acetone. 354 g (7 moles) of gaseous methyl chloride were introduced. During the reaction covering 5 to 6 hours, the temperature increased to 50° C. The precipitated crystals were separated form the mother liquor, washed with acetone and dried in a desiccator. 1202 g of acrylamidopropyltrimethylammonium chloride were obtained. This corresponds to a yield of 97%, relative to pure dimethylaminopropylacrylamide.

EXAMPLE II

Preparation of Methacrylamidopropyltrimethylammonium Chloride 1020 g (6 moles) of dimethylaminopropylmethacrylamide were pumped during 4 hours at 50° C. to a closed reaction vessel containing 5000 ml of acetone and 354 g (7 moles) of methyl chloride. The mixture was allowed to react for 4 hours. The vessel was opened and 1270 g of crystalline methacrylamidopropyltrimethylammonium chloride were recovered as in Example 1. This corresponds to a yield of 96%, relative to pure dimethylaminopropylmethacrylamide.

EXAMPLE III

Preparation of Acrylamidoneopentyltrimethylammonium Chloride 1104 g (6 moles) N,N,2,2-tetramethylaminopropylacrylamide and 354 g (7 moles) of methyl chloride were added to 5000 ml of acetone in a reaction vessel. The reactants were heated at 80° C. for 4 hours. The purification and recovery was performed as described in Example 1. 1238 g of product were obtained which corresponded to a yield of 88% relative to pure N,N,2,2 tetramethylaminopropylacrylamide.

EXAMPLE IV

Preparation of Acrylamidopropyltrimethylammonium Chloride 936 g (6 moles) of dimethylaminopropylacrylamide were fed during 4 hours at 60° C. to a closed reaction vessel containing 5000 ml of acetone and 354 g (7 moles) of methyl chloride. The mixture was allowed to react for 4 hours at 60° C. Purification and recovery was conducted as described in Example 1. 991 g of acrylamidopropyltrimethylammonium chloride were obtained which corresponded to a yield of approx. 80%.

What is claimed:

1. A process for producing a crystalline acrylamidoalkyltrialkylammohium chloride which comprises reacting a substituted acrylamide with alkyl chloride having 1 to 3 carbon atoms in the presence of a reaction medium selected from the group consisting of acetone, methyl tert. butyl ether and cyclohexane, said substituted acrylamide being represented by the formula:

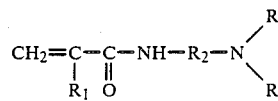

in which R is an alkyl radical having from 1 to 3 carbon atoms, $R_1$ is hydrogen or a methyl radical and R2 is a divalent alkylene radical having from 2 to 5 carbon atoms 2. A process according to claim 1 in which said substituted acrylamide is reacted with methyl chloride.

3. A process according to claim 1 in which said substituted acrylamide is dimethylaminopropyl methacrylamide and said product is methacrylamidopropyltrimethylammonium chloride.

4. A process according to claim 1 in which said substituted acrylamide is dimethylaminopropylacrylamide and said product is acrylamidopropyltrimethylammonium chloride.

5. A process according to claim 1 in which said reaction is conducted at a temperature ranging from ambient temperature to about 100° C.

6. A process according to claim 5 in which said reaction is conducted at a temperature ranging from about 40° C. to 80° C. and said reaction medium is acetone.

7. A process according to claim 1 in which said substituted acrylamide is dissolved in acetone and reacted with gaseous methyl chloride.

8. A process according to claim 1 in which said substituted acrylamide is added to a mixture of methyl chloride in acetone within a closed reactor.

* * * * *